(12) United States Patent
Grose

(10) Patent No.: US 10,751,227 B1
(45) Date of Patent: Aug. 25, 2020

(54) UNDERGARMENT LINER

(71) Applicant: Kia Grose, Temple Hills, MD (US)

(72) Inventor: Kia Grose, Temple Hills, MD (US)

(*) Notice: Subject to any disclaimer, the term of this patent is extended or adjusted under 35 U.S.C. 154(b) by 0 days.

(21) Appl. No.: 16/593,342

(22) Filed: Oct. 4, 2019

(51) Int. Cl.
*A61F 13/512* (2006.01)
*A61F 13/56* (2006.01)
*A61F 13/42* (2006.01)
A61F 13/539 (2006.01)
A61F 13/49 (2006.01)
A61F 13/493 (2006.01)

(52) U.S. Cl.
CPC ............ *A61F 13/512* (2013.01); *A61F 13/42* (2013.01); *A61F 13/5611* (2013.01); *A61F 13/493* (2013.01); *A61F 2013/422* (2013.01); *A61F 2013/49063* (2013.01); *A61F 2013/49066* (2013.01); *A61F 2013/53908* (2013.01); *A61F 2013/53966* (2013.01)

(58) Field of Classification Search
CPC .................. A61F 13/493; A61F 13/505; A61F 2013/49063; A61F 2013/49065; A61F 2013/49066; A61F 2013/51076; A61F 2013/53908; A61F 2013/53966; A61F 13/42; A61F 2013/422; A61F 2013/429
See application file for complete search history.

(56) References Cited

U.S. PATENT DOCUMENTS

| | | | |
|---|---|---|---|
| 6,013,066 A | 1/2000 | Samuelsson | |
| 6,409,712 B1 | 6/2002 | Dutari | |
| 6,524,290 B2 * | 2/2003 | Motta | A61F 13/474 604/385.01 |
| 6,623,466 B1 * | 9/2003 | Richardson | A61F 13/15211 604/385.11 |
| 9,066,835 B2 * | 6/2015 | Okawa | A61F 13/535 |
| 9,301,551 B2 | 4/2016 | Bach et al. | |
| 10,052,241 B2 * | 8/2018 | Richardson | A61F 13/15252 |
| 2011/0172627 A1 | 7/2011 | Mateo | |
| 2012/0157949 A1 * | 6/2012 | Knight | A61F 13/42 604/361 |
| 2013/0281945 A1 | 10/2013 | Gallo | |
| 2016/0302978 A1 * | 10/2016 | Lindstrom | A61F 13/4704 |

* cited by examiner

*Primary Examiner* — Catharine L Anderson
(74) *Attorney, Agent, or Firm* — The Law Firm of Andrea Hence Evans, LLC

(57) ABSTRACT

An embodiment of the undergarment can include an undergarment liner comprising a top layer; a bottom layer; an absorption layer; and a garment adhesive layer. The top layer can be oriented as the upper most layer and is the layer that comes in contact with the wearer of the liner. The absorption layer is oriented between the top layer and the bottom layer. The garment adhesive layer can comprise a coupling surface and an adhesion surface. The coupling surface opposes adhesion surface. The undergarment liner also comprises a first perforation line that extends through each layer and subdivides the undergarment liner into a plurality of subsections.

20 Claims, 5 Drawing Sheets

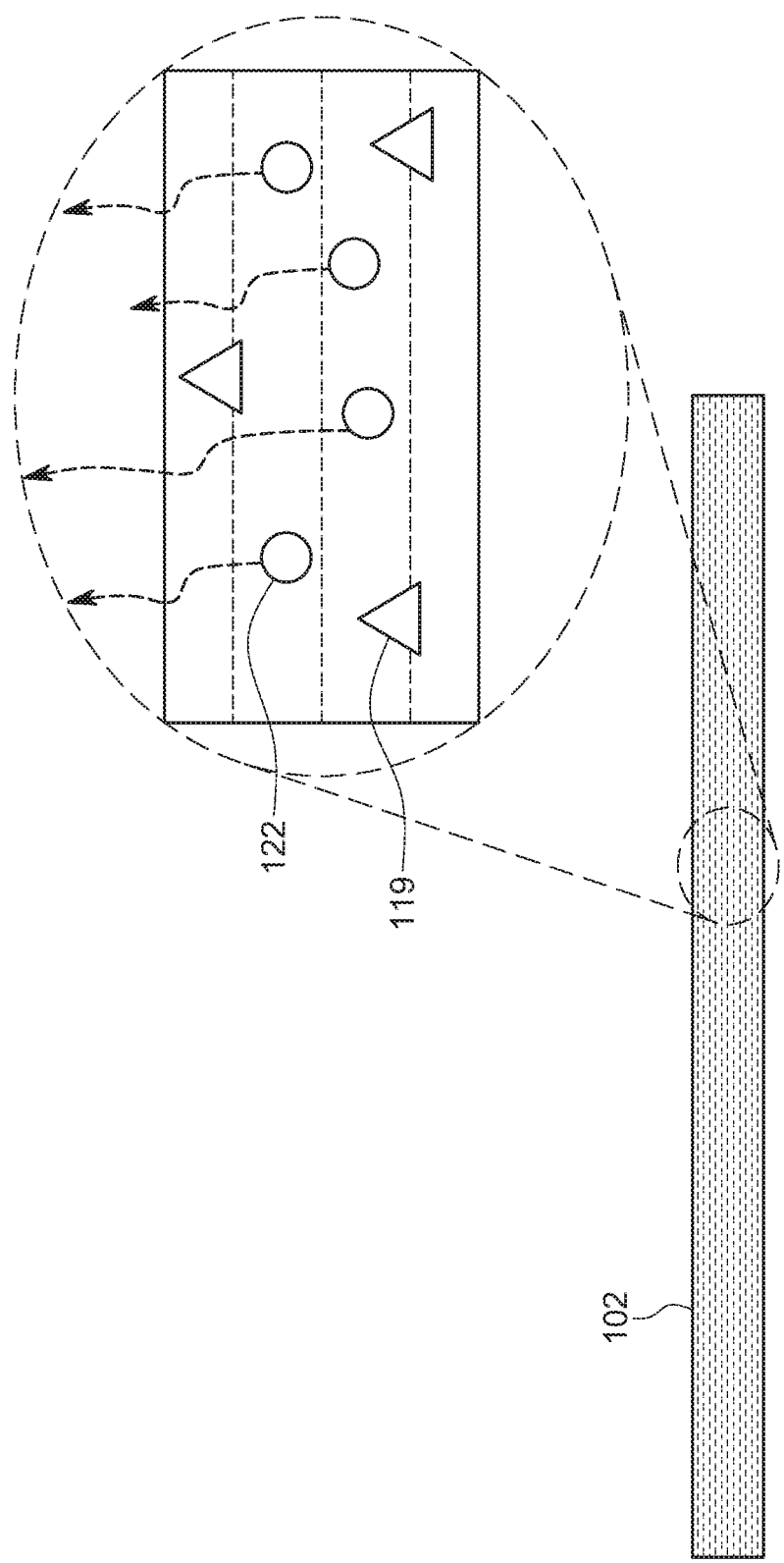

UNDERGARMENT LINER

TECHNICAL FIELD

The embodiments of this disclosure relate generally to an undergarment liner.

BACKGROUND

Leakage of bodily fluids in undergarments can be a result stemming from a persistent physical condition or a random accident. Ideally, a person at risk of experiencing these events may want to take precautions to prevent any discomfort from the leakage of bodily fluids. In previous embodiments, bulky materials may be used as a barrier between the body and the undergarment. Unfortunately, these bulky materials may provide discomfort and be visible. The products on the market have designed purpose and are not useful for multiple circumstances. For example, current undergarment liners for women may not be effective in preventing stains for men since the dimensions configurations attributed to anatomical differences. Further, the lack of any protection may cause the person experiencing the episode extreme emotional pain or embarrassment. Thus, a need exists for undergarment liners that are able to provide comfort and versatility to be used by both males and females of all ages and sizes. In addition, there is a need for undergarment liners that can be used in a variety of clothing types.

SUMMARY

Some or all of the above needs and/or problems may be addressed by certain embodiments of the disclosure. Certain embodiments of the disclosure can include an undergarment liner. An embodiment of the undergarment liner comprises a top layer; a bottom layer; an absorption layer; and a garment adhesive layer. The top layer can be oriented as the upper most layer and is the layer that comes in contact with the wearer of the liner. The absorption layer is oriented between the top layer and the bottom layer. The garment adhesive layer can comprise a coupling surface and an adhesion surface. The coupling surface opposes the adhesion surface. The undergarment liner also comprises a first perforation line that extends through each layer and subdivides the undergarment liner into a plurality of subsections. Alternatively, the adhesive layer does not require the perforation line.

Another embodiment of undergarment liner comprises a top layer; a bottom layer; an absorption layer; an outer layer; and a garment adhesive layer. The top layer can be oriented as the upper most layer and is the layer that comes in contact with the wearer of the liner. The absorption layer is oriented between the top layer and the bottom layer. The garment adhesive layer can comprise a coupling surface and an adhesion surface. The coupling surface opposes the adhesion surface. The undergarment liner also comprises a first perforation line that extends through each layer and subdivides the undergarment liner into a plurality of subsections. The outer layer can define a perimeter of the undergarment liner. The undergarment liner can be substantially 4 inches wide and substantially 6.5 inches long. The undergarment liner can also be constructed by embossing the layers together.

Other embodiments, features, and aspects of the disclosure are described in detail herein and are considered a part of the claimed disclosure. Other embodiments, features, and aspects can be understood with reference to the following detailed description, accompanying drawings and claims.

BRIEF DESCRIPTION OF THE DRAWINGS

FIG. 5 depicts a zoomed in cross-sectional view of a top layer from the undergarment liner in FIG. 2.

DETAILED DESCRIPTION

Figure 1:
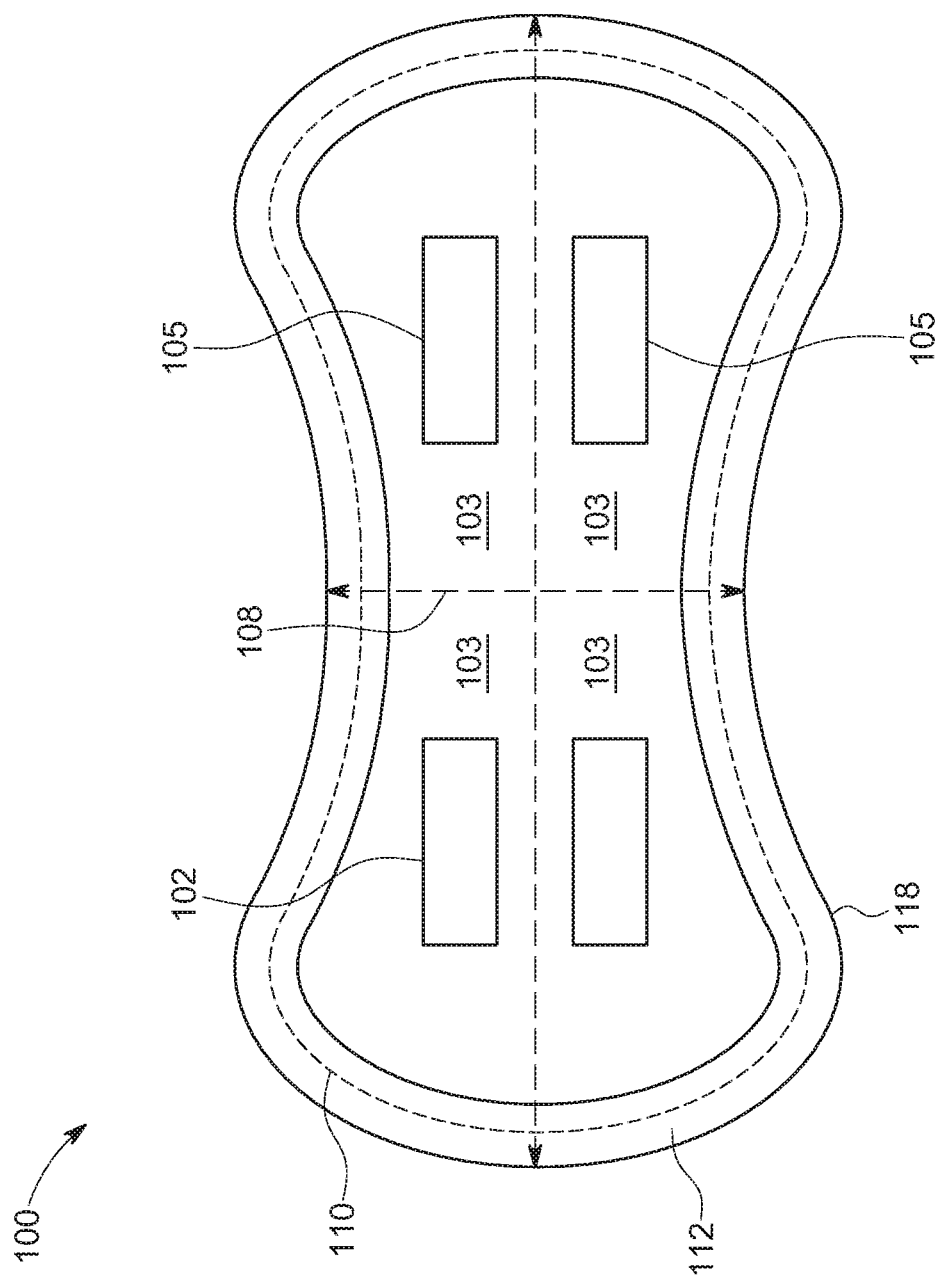
FIG. 1 depicts a top view of the undergarment liner.

Illustrative embodiments of the disclosure will now be described more fully hereinafter with reference to the accompanying drawings, in which some, but not all embodiments of the disclosure are shown. The disclosure may be embodied in many different forms and should not be construed as limited to the embodiments set forth herein; rather, these embodiments are provided so that this disclosure will satisfy applicable legal requirements.

Whenever appropriate, terms used in the singular also will include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," and "including" are interchangeable and not intended to be limiting. The term "such as" also is not intended to be limiting. For example, the term "including" shall mean "including, but not limited to."

The following description is provided as an enabling teaching of the disclosed articles, systems, and methods in their best, currently known embodiments. To this end, those skilled in the relevant art will recognize and appreciate that many changes can be made to the various aspects of the articles, systems, and methods described herein, while still obtaining the beneficial results of the disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to "a gasket" can include two or more such gaskets unless the context indicates otherwise.

As used throughout, "substantially" with respect to a measure can refer to a range of values comprising +/−10% or +/−10 degrees. For example, substantially orthogonal, normal, or parallel can include embodiments, where the referenced components are oriented +/−10 degrees of being classified as orthogonal, normal or parallel respectively.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

FIG. 1 depicts an embodiment of the disclosure. The embodiment of the undergarment liner 100 can comprise multiple layers to provide various levels of absorption for a potential leakage on the undergarment liner 100. The undergarment liner 100 can comprise at top layer 102, an absorption layer 104, a bottom layer 106, and a garment adhesive layer 107. In a further aspect, the undergarment liner 100 can be perforated into multiple subsections 103 along a perforation line 108. The embodiment can also include spacers 105 and an outer layer 112, where the outer layer 112 can define an outer perimeter of the undergarment liner.

Figure 3:
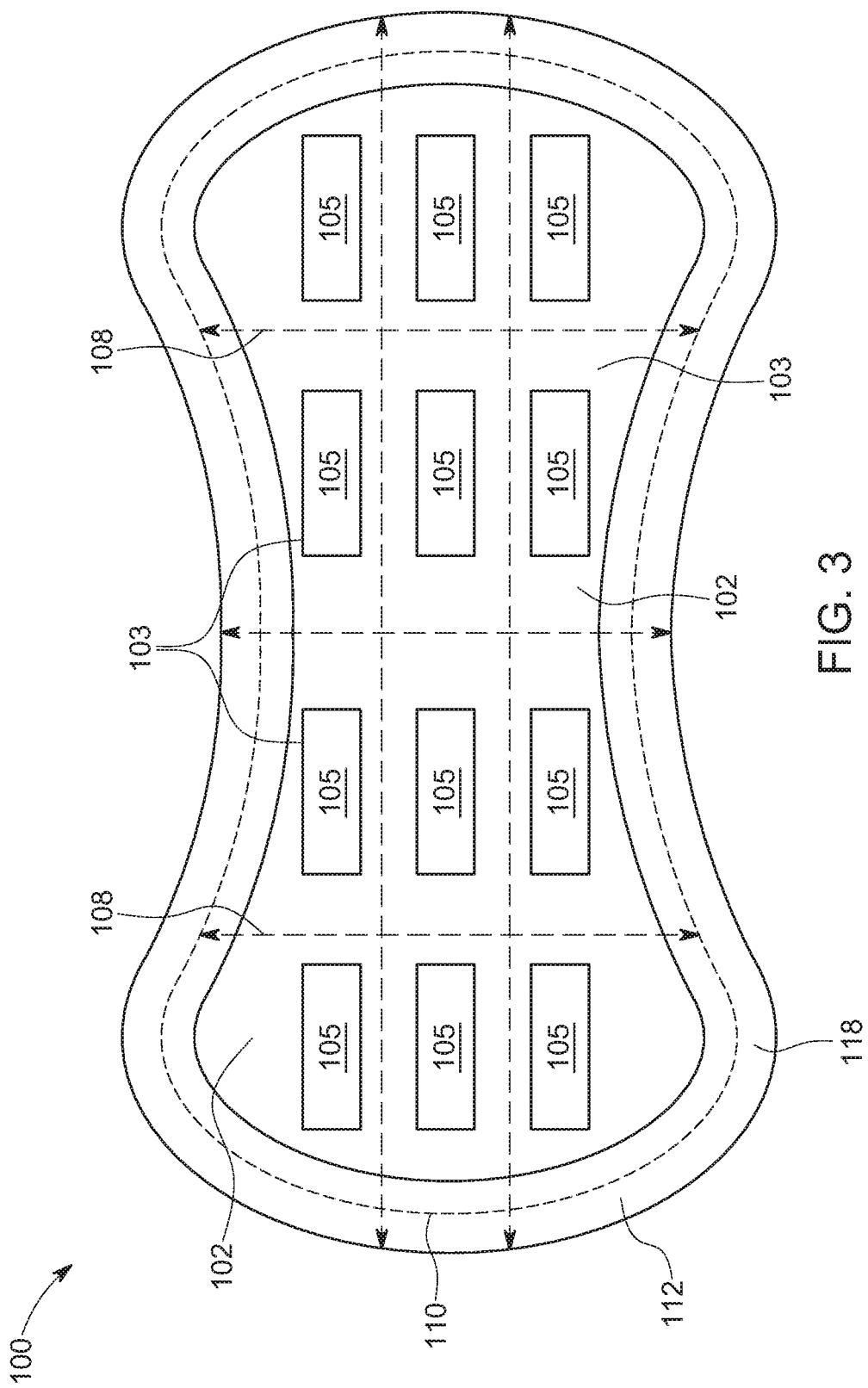
FIG. 3 depicts a top view of an alternative undergarment liner with multiple detachable subsections.

As shown in FIGS. 1 and 3, the undergarment liner 100 can be subdivided into different subsections 103. As shown in FIG. 1, the liner 100 can be further divided into two subsections up to N-number (See FIG. 3) of subsections based on the number of perforation lines 108 applied to the undergarment liner 100. For example, as shown in FIG. 1, the undergarment liner 100 can be divided into quadrants along perforation lines 108. The perforation lines 108 can be oriented in a perpendicular orientation. The perforation lines 108 facilitate an easier method of reshaping the perimeter of the undergarment liner 100 by tearing away unwanted subsections 103 along the perforation lines 108. In a further aspect, the orientation of the perforation lines 108 can be set on the undergarment liner 100 such that the undergarment liner is symmetrically portioned. In a further aspect the perforation lines can also be curved to provide additional customization. In a further aspect as shown in FIG. 3, additional perforation lines can be added to provide the undergarment liner with additional subsections. Accordingly, the additional subsections 103 will allow the wearer to further customize the undergarment liner 100 to address the potential variances in undergarments as well as preferred undergarment liner coverage of the undergarment, whereby the torn liner can be stacked on top of the remaining liner or permanently removed.

The liner can also be configured with a certain dimensions. In one aspect, the perimeter dimensions of the liner can comprise a minimum width of 3.5 inches and length of 6 inches. The liner can also be 4 inches wide and 6.5 inches long. A preferred dimensioning of the liner can comprise a width of 4 inches wide and length of 6.5 inches. The liner is sized in a way that it can be positioned parallel and on top of an undergarment or because of its width, the liner may be turned and positioned perpendicular to the undergarment below the liner.

As discussed earlier, the undergarment liner can comprise a top layer 102, absorption layer 104, and a bottom layer 106. Each of these layers can comprise materials that increase the absorption of liquids and reduce the thickness of the respective layer. For example, the layers can comprise but not be limited to woven cotton or synthetic cotton fibers, treated paper, hydro-activated gels, desiccants, and or other absorbent materials. In further aspects, these layers can comprise indicators that signal the depth of the leakage into an undergarment liner 100. In one aspect, the indicator can be a color change, based on the indicator coming in contact with a liquid. In a further aspect, adjacent layers can be configured to turn different colors when coming in contact with the liquid. For example, the top layer 102 can turn a shade of red, while the absorption layer 104 can turn a shade of blue. Viewed from the top, the resultant color would be purple, which would indicate to the wearer that the leakage extended at least two layers deep. Understandably, the colors used in the indicators can be adjusted to account for the natural coloration the fluids leaked (e.g. blood, urine, etc.). The overall translucence between adjacent layers can also be adjusted to provide a clearer result for color distinction; for example, by orientating the fibers of a respective layer in a different direction to allow additional light to pass through.

In a further aspect, the layers can exhibit varying levels of thickness. Any of the layers in the undergarment liner can range between about 0.05 mm to 5 mm. Accordingly, a reduced thickness of the layers can make the undergarment liner 100 more functional because the undergarment liner 100 can be easier to transport or stored, (e.g. in a purse or fanny pack). In one aspect, the top layer 102 and the bottom layer 106 can comprise thin ventilation sheets. As a ventilation sheet, layers 102 and 106 can provide moisture absorption. In addition, the ventilation sheets can allow for air to pass through the undergarment liner. The layers 102, 106 can have an arrangement of fibers that are arranged to facilitate air flow through the layers 102, 106 while still maintaining absorption capabilities. Allowing air to pass through the undergarment liner can decrease potential odors from liquids being locked within the absorption layer 104. Additionally, ventilation can help expedite drying of the undergarment liner in the event that the wearer is not able to immediately remove or exchange the undergarment liner 100.

The absorption layer 104 can comprise a substantial portion of a subsection 103. In an alternative aspect, the absorption layer 104 can comprise a smaller portion of the subsection 103. In a further aspect, the absorption layer 104 can comprise an absorption core 115. The absorption core 115 can be configured as a region within the absorption layer 104 with a concentrated amount of absorbent materials such as gels, woven fibers of cotton or similar material, or other more absorbent materials to further reduce leakage into adjacent layers below the absorption layer 104. In a further aspect, the fibers 111 can be treated to have more absorptive properties such as being treated to become hydrophilic.

Figure 4:
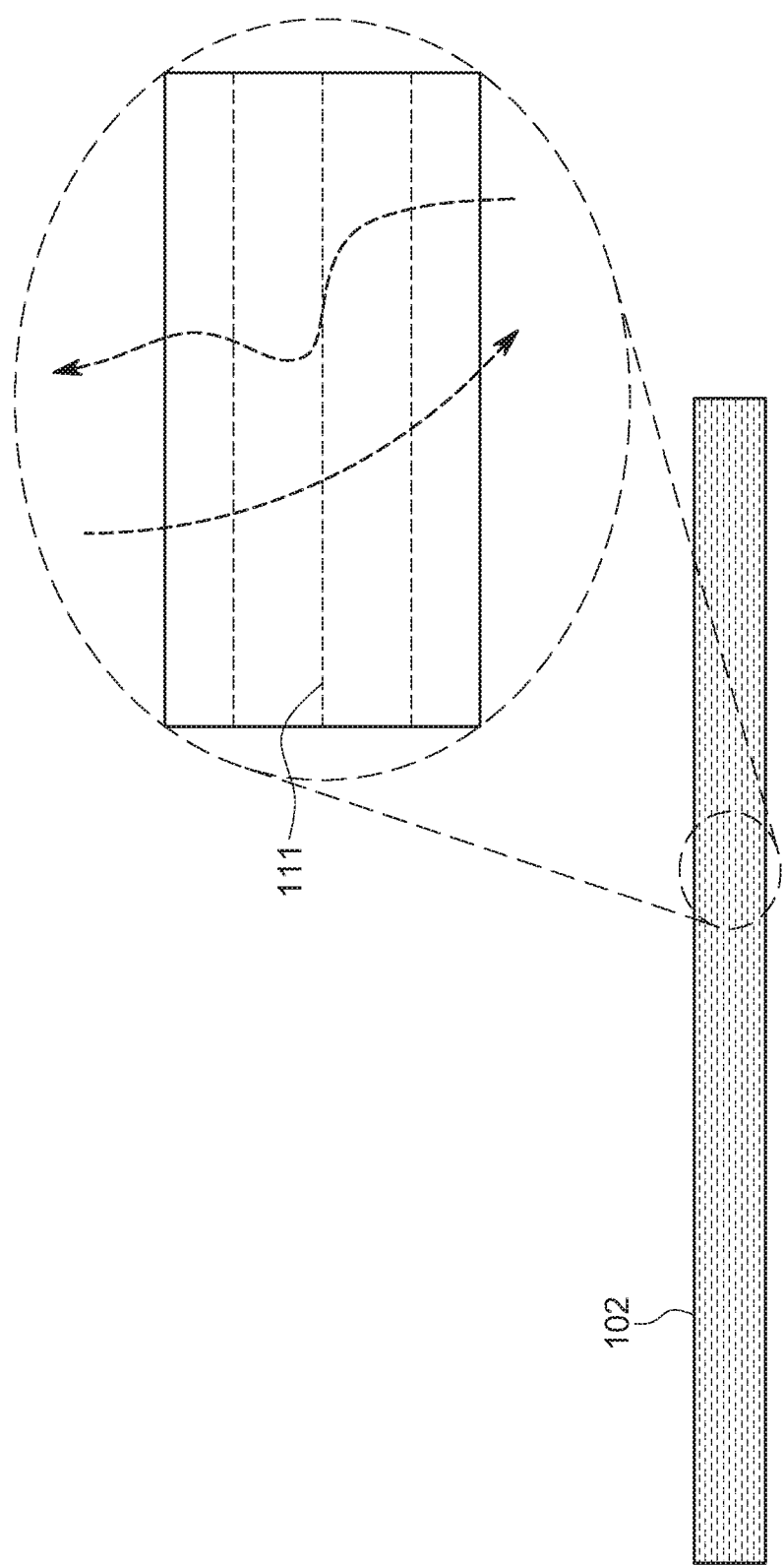
FIG. 4 depicts a zoomed in cross-sectional view of top layer from the undergarment liner in FIG. 2.

As shown in FIG. 4, the top layer 102 can comprise fibers 111 that are oriented in a first direction as shown by the directional lines of the pattern. In an alternative embodiment, the fibers 111 of the top layer 102 can be oriented in a second direction. In a further aspect, the orientation of the fibers in any layer can facilitate the movement of liquid through a layer to an adjacent lower layer. For example, the fibers in the top layer 102 can be oriented in a first direction and the fibers in the absorption layer 104 can be oriented in a second direction. In one embodiment, a layer can have one subset of fibers oriented in a first direction and a second subset of fibers oriented in a second direction. In yet another embodiment, the fibers or materials in respective layers can be oriented in a randomized pattern to reduce the potential spacing between the fibers of layers, as liquid flows through the respective layers. Similarly, the orientation of the fibers in the top layer 102 and/or the orientation of absorption layer 104 can facilitate the fluid flow to the absorption core 115. It should be understood that any combination of fiber arrangement is possible for each of the respective layers of the undergarment liner 100. It should also be considered that instead of fibers 111, other absorbent materials can be used; similarly, these absorbent materials can be formed and/or oriented to yield the same liquid channeling capabilities as the fibers.

Figure 2:
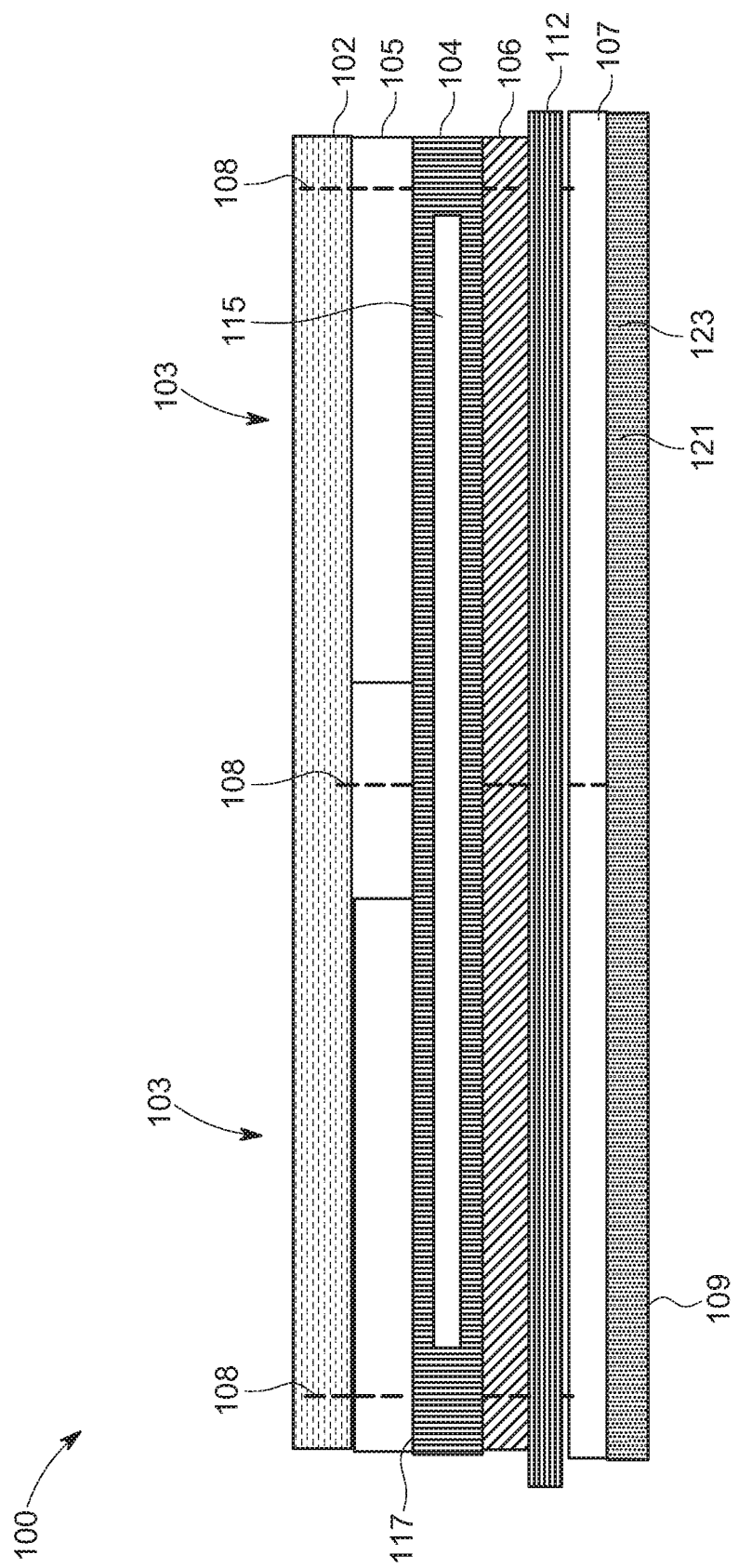
FIG. 2 depicts a cross-sectional side view of the undergarment liner in FIG. 1.

As shown in FIG. 1 and FIG. 2, the undergarment liner can further comprise spacers 105. The spacers 105 can be oriented between the top layer 102 and the absorption layer 104. The spacers 105 can facilitate additional ventilation between the top layer 102 and the absorption layer 104. The spacers can be an embossed material that covers a portion of the subsection 103. Similar to the other layers, the spacers can comprise absorbent materials, such as but not limited to, hydrophilic fibers, woven fibers, absorbent gels, paper, or desiccants. The spacers can also comprise a thickness from about 1 mm to 5 mm. In another aspect, the spacer 105 can span the entire subsection 103. In a further aspect, the spacers can also comprise porous or compressible resilient materials, such as a sponge or foam composite. The compressible resilient material deforms in response to a compressive force and return to their original shape when the compression force is removed.

As shown in FIG. 5, each of the layers can comprise additional aspects that are customized for various levels of skin sensitivity and moisture. For examples, the top layer 102 can comprise a hypoallergenic additive 119 to reduce potential irritation to the wearer. In another aspect, a fragrance emitting material can be dispersed in any layer. The fragrance emitting material 122 can be hydro-activated, such that a liquid acts as a catalyst and causes the fragrance emitting material to release a pleasant fragrance after the material 122 comes in contact with a liquid.

The various layers can be attached by various means. For example, the top layer 102 and the absorption layer 104 can be coupled to the bottom layer 106 by stitching. In an alternative aspect, the undergarment liner 100 can further comprise an adhesive 117. The adhesive 117 can be between any of the layers to attach adjacent layers and/or spacers 105 to each other. Structurally, the adhesive 117 can be hydrophobic, so that the adhesive 117 does not dissolve the bonds between adjacent layers when a liquid comes in contact with the adhesive 117. In another alternative aspect, the adhesive 117 can be hydrophilic, wherein the adhesive may have the ability to dissolve in water over time, but the adhesive 117 may be placed at the corners or other arrangement that allows adhesion between the layers.

In another aspect, the outer layer 112 of the undergarment liner 100 can comprise a perimeter edge that is manipulated to also adjust the surface area of the undergarment liner coverage. For example, as discussed earlier, subsections 103 can be removed to change the external perimeter of the undergarment liner 100. Here, the external perimeter can be adjusted by removing the outer sections 118 of the outer layer 112 along a perimeter perforation line 110. Removing the outer section 118, provides another possibility for customization of the undergarment liner 100, similar to removing subsections 103.

The garment adhesive layer 107 can be used to attach the undergarment liner 100 to the garment. In one aspect, the bottom layer 106 can be attached to a garment adhesive layer 107. In an alternative embodiment, the garment adhesive layer can be attached to the outer layer 112. The garment adhesive layer 107 can be comprised of adhesives on both sides of the layer 107. One side of the layer garment adhesive layer 107 can be attached to the undergarment liner 100, and the other side can be used to attach the undergarment liner to the desired region on a garment. In a further aspect, the undergarment liner 100 can comprise an adhesive cover sheet 109. The adhesive cover sheet 109 reduces unintentional attachment of the undergarment liner 100 to an incorrect surface. The mating surface 123 of the adhesive cover sheet 109 can protect the adhesive surface 121 of the garment adhesive layer 107. When the wearer decides where the liner 100 should be placed in their undergarments, the adhesive cover sheet 109 can be removed, exposing the adhesive surface 121 for attachment.

While certain embodiments of the disclosure have been described in connection with what is presently considered to be the most practical and various embodiments, it is to be understood that the disclosure is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the disclosure, including the best modes, and also to enable any person skilled in the art to practice certain embodiments of the disclosure, including making and using any devices or systems and performing any incorporated methods. The patentable scope of certain embodiments of the disclosure is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An undergarment liner comprising:
a top layer comprising a first leakage indicator; a bottom layer; an absorption layer comprising a second leakage indicator; and a garment adhesive layer; wherein the top layer is oriented to interface with a wearer of the undergarment liner; the absorption layer is oriented between the top layer and the bottom layer; wherein the garment adhesive layer comprises coupling surface and an adhesion surface, wherein the coupling surface opposes adhesion surface; and wherein the undergarment liner comprises a first perforation line that extends through each layer and subdivides the undergarment liner into a plurality of subsections; and the first leakage indicator and the second leakage indicator are configured to provide a wearer an indication of leakage depth between at least the top layer and the absorption layer.

2. The undergarment liner of claim 1, wherein the first perforation line is oriented along a first axis, wherein the first axis divides the undergarment liner into a first grouping of subsections.

3. The undergarment liner of claim 2, wherein the undergarment liner comprises a second perforation line oriented along a second axis, therein the second axis subdivides the first grouping of subsections into a second grouping of subsections.

4. The undergarment liner of claim 1, further comprising an interlayer adhesive, wherein the interlayer adhesive is oriented between at least two of the layers.

5. The undergarment liner of claim 1, wherein at least two of the layers are coupled by stitching.

6. The undergarment liner of claim 1, wherein the absorption layer further comprises an absorption core.

7. The undergarment liner of claim 1, wherein at least one layer comprises a hypoallergenic additive.

8. The undergarment liner of claim 1, wherein at least one layer comprises a hydro-responsive fragrance emanating material.

9. The undergarment liner of claim 1, wherein at least one of the layers comprises a plurality of fibers comprising a first subset of the plurality of fibers and a second subset of the plurality of fibers.

10. The plurality of fibers of claim 9, wherein the first subset is oriented in a first direction.

11. The plurality of fibers of claim 10, the second subset is oriented in a second direction.

12. The garment adhesive layer of claim 1, wherein the coupling surface is attached to the bottom layer and the adhesion surface is oriented to adhere to an undergarment worn be the wearer.

13. The undergarment liner of claim 1, further comprising an adhesive cover sheet comprising a protection surface, wherein the protection surface is adjacent to the adhesion surface of the garment adhesive layer.

14. The undergarment liner of claim 1, further comprising an outer layer that comprises a perimeter perforation line proximal to the perimeter of the undergarment liner, wherein the perimeter perforation line defines an area for a detachable outer perimeter section of the undergarment liner.

15. The undergarment liner of claim 14, wherein the outer layer is oriented between the bottom layer and the garment adhesive layer.

16. The undergarment liner of claim 15, wherein the coupling surface of the garment adhesive layer is attached to the outer layer and the adhesion surface is oriented to adhere to an undergarment worn by the wearer.

17. The undergarment liner of claim 1, further comprising a spacer, wherein the spacer is oriented between the top layer and the absorption layer.

18. An undergarment liner comprising:

a top layer comprising a first leakage indicator; a bottom layer; an absorption layer comprising a second leakage indicator; a garment adhesive layer, and an outer layer; wherein the top layer is oriented to interface with a wearer of the undergarment liner; the absorption layer is oriented between the top layer and the bottom layer; wherein the garment adhesive layer comprises coupling surface and an adhesion surface, wherein the coupling surface opposes adhesion surface; and wherein the undergarment liner comprises a first perforation line that extends through each layer and subdivides the undergarment liner into a plurality of subsections; wherein the outer layer defines an outer perimeter of the undergarment liner; wherein the undergarment liner is substantially 4 inches wide and substantially 6.5 inches long; and wherein the first leakage indicator and the second leakage indicator are configured to provide a wearer an indication of leakage depth between at least the top layer and the absorption layer.

19. The undergarment liner of claim 18, further comprising a spacer, wherein the spacer is oriented between the top layer and the absorption layer.

20. The undergarment liner of claim 18, wherein the outer layer is defined by a perimeter perforation line, and the outer layer can be removed from the undergarment liner along the perimeter perforation line.

* * * * *